United States Patent
Feng et al.

(10) Patent No.: US 12,188,889 B2
(45) Date of Patent: Jan. 7, 2025

(54) SYSTEM AND METHOD FOR CONTINUOUSLY AND INTELLIGENTLY MEASURING WATER CONTENT OF SUBGRADE IN REAL TIME

(71) Applicant: SHIJIAZHUANG TIEDAO UNIVERSITY, Hebei (CN)

(72) Inventors: Huaiping Feng, Hebei (CN); Hui Zhao, Hebei (CN); Deliang Ma, Hebei (CN); Jianmei Chang, Hebei (CN); Bing Duan, Hebei (CN); Chaoliang Ye, Hebei (CN); Yucheng Zhao, Hebei (CN)

(73) Assignee: SHIJIAZHUANG TIEDAO UNIVERSITY, Shijiazhuang (CN)

( * ) Notice: Subject to any disclaimer, the term of this patent is extended or adjusted under 35 U.S.C. 154(b) by 457 days.

(21) Appl. No.: 17/630,847

(22) PCT Filed: Nov. 13, 2019

(86) PCT No.: PCT/CN2019/118137
§ 371 (c)(1),
(2) Date: Jan. 27, 2022

(87) PCT Pub. No.: WO2021/017309
PCT Pub. Date: Feb. 4, 2021

(65) Prior Publication Data
US 2022/0341862 A1   Oct. 27, 2022

(30) Foreign Application Priority Data
Jul. 29, 2019   (CN) .......................... 201910690469.5

(51) Int. Cl.
*G01N 27/04*   (2006.01)
*E01C 19/28*   (2006.01)
(Continued)

(52) U.S. Cl.
CPC ........... *G01N 27/04* (2013.01); *E01C 19/288* (2013.01); *E01C 23/01* (2013.01); *G01N 33/42* (2013.01)

(58) Field of Classification Search
CPC ....... G01N 33/24; G01N 27/02; G01N 33/246
See application file for complete search history.

(56) References Cited

U.S. PATENT DOCUMENTS 3,646,437 A    2/1972  Nutter
6,484,652 B1 *  11/2002  Colburn, Jr. ......... A01C 21/007
47/1.3

(Continued)

FOREIGN PATENT DOCUMENTS

CN    104897734 A    9/2015
CN    106404845 A    2/2017

(Continued)

OTHER PUBLICATIONS

Apr. 26, 2020 Search Report issued in International Patent Application No. PCT/CN2019/118137.

*Primary Examiner* — Jermele M Hollington
*Assistant Examiner* — Temilade S Rhodes-Vivour
(74) *Attorney, Agent, or Firm* — Oliff PLC

(57) ABSTRACT

A test system and test method continuously and intelligently measures water content of subgrade in real time. The test system is based on the theory of resistivity, and is equipped with a wheeled machine to measure the water content of subgrade. The wheeled machine includes scroll roller. The test system includes: at least one set of electrode including four probes wherein detection parts of the four probes are linearly and equidistantly arranged on the scroll roller. The arrangement direction of the detection parts of the four probes is parallel to the axis of the scroll roller; a data integration apparatus is connected to the four probes and used for performing data calculation, analysis, and trans- (Continued)

mission; the electric source is connected to data integration apparatus and used for supplying a working current. The system and method can realize automatic signal collection, non-destructive detection of subgrade soil and dynamic water content measurement.

22 Claims, 2 Drawing Sheets

(51) Int. Cl.
*E01C 23/01* (2006.01)
*G01N 33/42* (2006.01)

(56) References Cited

U.S. PATENT DOCUMENTS

| | | | |
|---|---|---|---|
| 8,159,357 B1* | 4/2012 | Jarvinen | G01V 9/02 340/580 |
| 10,082,492 B2* | 9/2018 | Mazzeo | G01N 17/02 |
| 2016/0050902 A1* | 2/2016 | Crisp | A01M 19/00 43/124 |
| 2018/0168094 A1* | 6/2018 | Koch | G01J 5/0875 |
| 2019/0059209 A1* | 2/2019 | Brune | G01N 33/24 |

FOREIGN PATENT DOCUMENTS

| | | |
|---|---|---|
| CN | 109613067 A | 4/2019 |
| CN | 109898391 A | 6/2019 |
| CN | 110243875 A | 9/2019 |

* cited by examiner

SYSTEM AND METHOD FOR CONTINUOUSLY AND INTELLIGENTLY MEASURING WATER CONTENT OF SUBGRADE IN REAL TIME

PRIORITY

The present invention claims the priority of the Chinese patent application No. CN201910690469.5 filed on Jul. 29, 2019 and entitled "A system and method for continuously and intelligently measuring water content of subgrade in real time". All of their documents are incorporated into the present invention by references.

TECHNICAL FIELD

The invention relates to the technical field of measuring water content of soil, in particular, to the field of measuring water content of subgrade.

TECHNICAL BACKGROUND

Subgrade refers to a strip-shaped structure which is built as a pavement foundation based on route location and a certain technical requirement, is the foundation of railway and highway and is a linear structural object built with soil or stone, etc. In terms of materials, subgrade can be divided into three types: soil subgrade, stone subgrade and earth rock subgrade.

In the process of subgrade compaction, the water content of filler is an important index that affects overall quality of subgrade, and also has a profound significance for the study of the complex characteristics of the compacted soil. The existing intelligent compaction system of subgrade is based on the vibration response mechanism between the subgrade structure and scroll roller of road compacting machine. The objective of controlling compaction quality of subgrade can be achieved by measuring the compaction force characteristics of subgrade soil. However, in the process of compacting subgrade, the water content of filler also plays an indispensable role in compaction quality. Therefore, it is necessary to establish a test system for continuously and intelligently measuring water content of subgrade in real time which is extremely important value to perfect the intelligent compaction system of subgrade.

The methods of measuring water content of soil body are divided into a direct test method and an indirect test method. The direct test method comprises drying method, alcohol combustion method and the like. These traditional test methods are not able to continuously and dynamically measure and the measurement range is relatively limited. Therefore the applied universality of the methods is not high in the process of subgrade compaction. Indirect test method is to measure a certain indirect variable quantity that affects the soil water content, and establish a theoretical relationship between the indirect variable quantity and the water content, so as to obtain the water content. The method comprises neutron emission method, time-domain reflectometery method, geological radar method, an electrical resistivity method and the like. When the water content of soil body by neutron emission method and time-domain reflectometer method, the sensors need to be calibrated repeatedly by professional personnel and the measurement range is smaller so that the field practicability is limited due to the higher accuracy requirements. The detection technology of geological radar method on site shows low sensitivity and defect of poor visibility from the measured results of water content and the like, leading the technology difficult to popularize and apply in engineering.

In view of this, it is necessary to develop a technology capable of continuously and accurately measuring water content of subgrade in real time.

SUMMARY OF THE PRESENT INVENTION

The invention aims to provide a test system and test method for continuously and intelligently measuring water content of subgrade in real time in order to continuously and accurately measure water content of subgrade in real time.

In order to achieve the above purpose, in one aspect of the present invention is to provide technical solutions as follows:

A test system for continuously and intelligently measuring water content of subgrade in real-time, is equipped with a wheeled machine comprising a scroll roller to detect water content of subgrade according to electrical resistivity theory comprising:

at least a set of electrode comprising four probes, the detection parts of the four probes are linearly arranged on the scroll roller, and the arrangement direction of the detection parts of the four probes is parallel to the axis of the scroll roller;

a data integration apparatus is respectively connected to the four probes used for data calculation, analysis and data transmission;

and an electric source is connected to the data integration apparatus used for providing working current.

In another aspect of the present invention, the present invention provides the technical solutions as follows:

A test method for continuously and intelligently measuring water content of subgrade in real-time, is applied to the test system comprising the following steps:

when a set of electrode gets in touch with soil body, probe a, probe b, probe c and probe d of the set of electrode come into contact with subgrade soil with different water content during the scroll roller of the road compacting machine's moving process. The probe a and probe d are connected to the constant current source, voltage $U_{bc}$ between probe c and probe d, and electric potential difference $U_s$ at both ends of a standard electric resistance $R_s$ are measured through the data integration apparatus so that the measured electric resistance can be calculated:

$$R_t = \frac{U_{bc}}{\frac{U_s}{R_s}}$$

ρ can be obtained according to the formula:

$$\rho = \frac{d_{ab}(d_{ab} + d_{bc})}{d_{bc}} \pi R_t$$

where $d_{ab}$ and $d_{bc}$ are the distances between the probe a and probe b, the probe b and probe c respectively; $d_{ab}=d_{cd}=nd_{bc}$, where n is a positive integer; ρ electrical resistivity of subgrade soil is calculated; the water content is determined according to the corresponding relationship between the pre-calibrated electrical resistivity and the water content so that the water content of subgrade soil at any position is obtained.

In conclusion, a continuous intelligent measurement of water content of subgrade soil in real time can be achieved in the present invention using electrical resistivity theory (Wenner's theory) because the probes follow along with the scroll roller's moving.

The probes fixed on the scroll roller can bear the same vibration pressure as the scroll roller does in order to ensure the connectivity with the soil body, and the shape of top end of the probes is made of 1-2 mm round protrusion in order to continuously and intelligently measuring water content in real time, so the accuracy is greatly improved and subgrade compaction quality is comprehensively controlled, and further possibly realizing automatic signal acquisition, nondestructive measurement and dynamic measurement of water content of subgrade soil.

DETAILED DESCRIPTION OF THE EMBODIMENTS

The present invention is further illustrated in detail in the light of the drawings and embodiments as follows.

Figure 1:
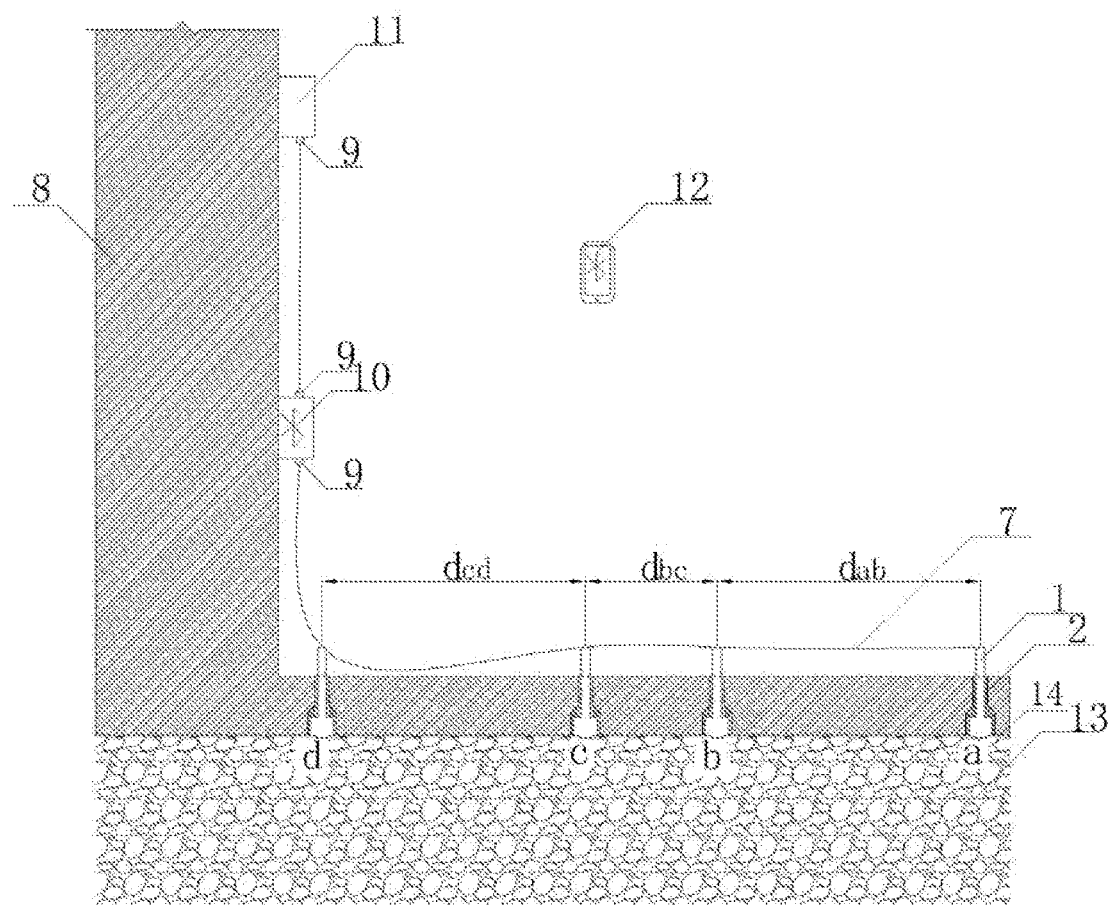
FIG. 1 is a schematic diagram of the devices of an embodiment according to the system of the present invention.
Figure 2:
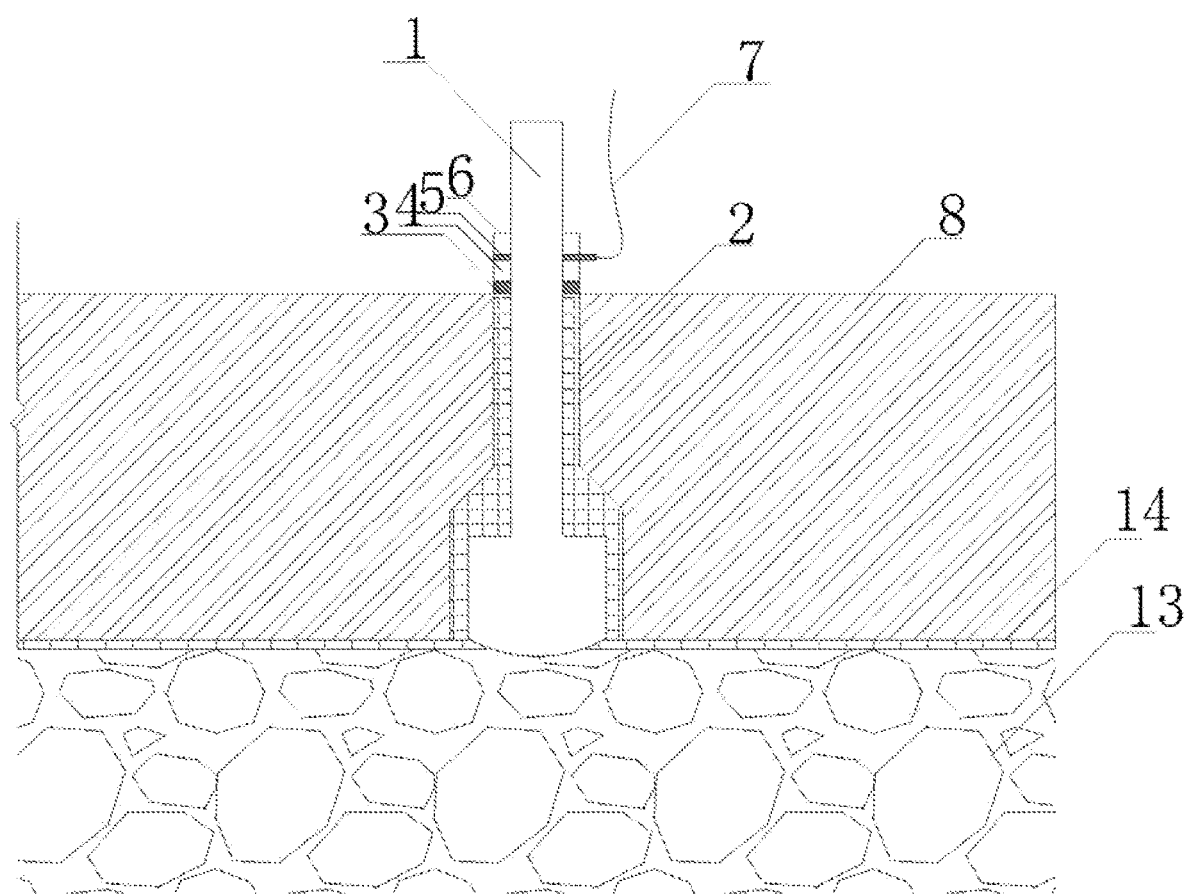
FIG. 2 is a structural schematic diagram of a probe of an embodiment according to the system of the present invention.

As shown in FIG. 1 and FIG. 2, the system embodiment of the present invention comprises at least a set of electrode 1 (four probes), a data integration apparatus 10 used for intelligently measuring water content, a constant current source 11 as an electric source, and a visible mobile device 12 facilitating data acquisition in real time and sending operation command instruction, wherein the probe 1 and the constant current source 11 are all electrically connected with the data integration apparatus 10 via wire 7. The data integration apparatus 10 has a built-in wireless communication module which is in wireless communication connection with the visible mobile device 12.

In order to clearly describe the contact condition between the probes and the subgrade soil, FIG. 1 also shows the subgrade soil 13. When measuring water content, the four probes 1 are fully contact with the subgrade soil 13 measured due to the protrusion of top end (outer end).

A set of electrode 1 comprises four probe a, b, c and d, all of which have a certain strength. They are fixed on the scroll roller 8 of the road compacting machine through preset holes, which can bear the pressure during the machine's moving process and the vibration pressure during the vibration compaction. Moreover, the top of each probe 1 has a circular protrusion of 1-2 mm to ensure full contact with the subgrade soil 13. Preferably, the detection parts of the four probes are arranged in a straight line arrangement and equidistantly arranged on the scroll roller 8.

As detailed in FIG. 2, an insulation isolation layer 2 is provided between the probe a, probe b, probe c, probe d and the preset holes of the scroll roller 8, the arrangement direction of the detection parts of the four probes is parallel to the axis of the scroll roller 8; The insulation isolation layer 2 adopts a hard insulation material such as Teflon or the like. The extending part of the outer ends of probe a, probe b, probe c and probe d protruding out of the inner surface of scroll roller 8 is firstly provided with insulation gasket 3 which is fixed by nut 4. Next, the wire terminal 5 is configured, and then the wire terminal 5 is fixed by nut 6 and is connected with one end of a signal wire 7, and the four signal wires 7 are a plurality of twisted copper wires in a four core shielding cable. Probe a, probe b, probe c and probe d are parallel distributed on the scroll roller 8. Preferably, the distance between the adjacent probes in the four probes is equidistantly spaced, and the connecting line of the four probes is parallel to the axis of the scroll roller 8, so as to ensure that the four probes 1 simultaneously touch the subgrade soil 13.

Preferably, within the test influence range of 100 cm long and 50 cm wide of outer surface of scroll roller 8, except for the outer end surface of probe 1, an insulation coating 14 with thickness of about 2 mm shall be applied onto other range to eliminate the influence of the outer surface of scroll roller 8 on the test potential Certainly, the insulation coating 14 of the other range may also be an option.

Further, the signal wire 7 is placed into the hard PE pipe to avoid exposure, and the hard PE pipe is arranged on the inner surface of the scroll roller 8 with a clamp.

Furthermore, the probe 1 is a titanium-iron alloy with good conductivity, and its cross section adopts a special shape: the diameter of the outer part is large, the diameter of the inner part is small, which is conducive to bear the impact vibration pressure and maintain the full contact between the probe 1 and the subgrade soil 13. Each probe 1 is a screw-rod structure. The length of each probe 1 is 60 mm, the diameter of its lateral section is 20 mm, the diameter of its inner section is 6 mm. The length of its outer side is 12 mm, the length of its inner side is 48 mm, the length of the part extending out of its inner surface of the scroll roller 8 is 20 mm, and the length of its thread part is 20 mm.

Further, the outer insulation layer of probe 1 also adopts a specially-made shape. In order to reduce the impact of shear damage at the contact place between the insulation layer and the probe, the transition form is appropriately changed.

Furthermore, an insulation gasket 3 is firstly provided to prevent the probe from forming an equipotential body on the inner surface extending out of the scroll roller 8.

Next, the nut 4, the wire terminal 5 and the nut 6 are successively configured. The wire terminal 5 is ring shape of copper and is welded with the signal wire 7.

The signal wire 7 connecting the probe 1 and the data integration apparatus 10 is preferably an enameled wire made of single-branch multi-stranded pure copper wire, and the specific specification of which is preferably 4×0.75 individual shielding signal wire. The outer side of each shielding wire is copper winding wire which improves the individual shielding ability. The outer side is protected by silicone rubber, the total thickness of 0.3 mm thereof, to ensure the high strength, superconductivity and high flexibility of the cable.

The test signal of the test probe 1 converges at the signal input port of the data integration apparatus 10 via the wire 7. The data integration apparatus 10 has the functions of test data acquisition, calculation, analysis and wireless transmission of water content of subgrade soil. The internal part of the data integration apparatus 10 is preferably an integrated circuit, which mainly comprises a standard electric resistance, a voltmeter, an ammeter (devices necessary for the implementation of the Wenner's theory), and a wireless transmission module in addition. The voltmeter determines the electric potential of the standard electric resistance and the electric resistance of probes b, probe c contacting the subgrade soil 13. The ammeter determines the electric current passing through electric resistance of the subgrade soil, and the wireless transmission module transmits the data to the visible mobile device 12. The constant current source 11 is preferably a nickel hydrogen battery, and is connected with the data integration apparatus 10 through electric conductive joint 9 for providing a constant current to the data integration apparatus 10. However, the visible mobile device 12 is provided with a built-in application program APP (the development process of APP commonly used by the mobile devices has been mature, and the detailed will not be described herein). After authorization and approval, it is possible of measuring water content of subgrade soil 13 by clicking on "continuous test".

The APP for measuring water content can provide two buttons. The "connection device" provides function of real-time connection authorization, and the "continuous measurement" provides the function of automatically computing data into Resistivity folder. Display interface of water content can realize real-time visualization of the water content.

The data integration apparatus 10 and the constant current source 11 are both placed in a resin square box with a suitable size, wherein the two ends of the box wall of the data integration apparatus 10 are respectively provided with preset holes, while the one end of the box wall of the constant current source 11 is only provided with preset holes which is specially used for fixing the electric conductive joint 9, preferably is a four-wired joint. The two square boxes are fixed onto the inner surface of scroll roller 8 by a clamp.

In the embodiment of present invention, the soil electrical resistivity is tested according to the Wenner's theory. Probe a, probe b, probe c and probe d are inserted into scroll roller 8 of road compacting machine. When the probes contact soil, the constant current is applied between probe a and probe d, and a voltage is generated on the standard electric resistance and the other two electrodes, according to the theory. The detailed operation steps are as follows:

Following the scroll roller of road compacting machine's moving process, when probe a, probe b, probe c and probe d contact subgrade soil 13 with different water content, the visible mobile device 12 is connected, clicking on the "continuous measurement" command button to connect probe a and probe d with the constant current source 11, and measuring the potential difference Us at both ends of the standard electric resistance Rs and the voltage Ubc between probe c and probe c through the voltmeter of the data integrated circuit 10. From this, the test electric resistance can be calculated by the following formula:

$$R_t = \frac{U_{bc}}{\frac{U_s}{R_s}}$$

ρ can be obtained according to the formula:

$$\rho = \frac{d_{ab}(d_{ab} + d_{bc})}{d_{bc}} \pi R_t$$

Generally, $d_{ab}=d_{cd}=nd_{bc}$ where n is a positive integer; the electrical resistivity of subgrade soil P is calculated out by programming in integrated circuits, Due to the relationship between the electrical resistivity of soil body and water content is affected by air temperature, the present invention established relationship formula between electric resistivity and water content relationship considering the influence of temperature as follows:

$$\omega = a \ln[b(0.45+1.4e^{-t/27})\rho]$$

Among them, a,b is the relation parameters of electrical resistivity and water content affected by different soil properties, is necessary to carry out calibration test of soil samples with no less than four equal differential water content (such as 4%, 6%, 8%, 12%) under a predetermined compaction at room temperature of 25 degree before construction to determine the parameters a,b; t is the air temperature in real time during compaction, the specific specification of which is ° C.; ρ is the electrical resistivity of soil body obtained through the test of the present invention.

Finally, the water content of the subgrade is determined according to the corresponding relationship between pre-calibrated electric resistivity and water content of soil body, so as to obtain the water content of the subgrade soil at any position of the subgrade which is saved in the Resistivity folder for uploading and summarizing.

In conclusion, the present invention has achieved a continuous intelligent test of subgrade water content in real time based on the Wenner's theory due to the adoption of the probes with a certain hardness possible of which directly contact subgrade soil under the vibration load. The test precision of water content of subgrade soil is greatly improved. It has the advantages of a real-time, continuous, non-destructive damage, visualization and the like. Further it combines water content with the intelligent compaction system. In particular, the shape design of the probes is reasonable, and the insulation property between the probes and scroll roller is good.

The influence of test error is reduced. The mobile equipment can control the test system remotely, further control the compaction quality. The operation of the present invention is simple and the test range is no long limited. The quality control level of subgrade compaction is tremendously improved.

It can be known from the general technical knowledge that the present invention can be realized by other embodiments without departing from its spiritual essence or necessary features thereof. Therefore, the disclosed above-mentioned embodiments are only examples for explanation in various aspects, not the only ones. All changes within the scope of the present invention or within the equivalent scope of the present invention are all encompassed in the present invention.

The invention claimed is:

1. A test system for continuously and intelligently measuring water content of subgrade in real-time, equipped with a wheeled machine comprising a scroll roller to detect water content of subgrade according to electrical resistivity theory, the system comprising:
   at least a set of electrodes comprising four probes, whereby detection parts of the four probes are linearly and equidistantly arranged on the scroll roller, and the arrangement direction of the detection parts of the four probes being parallel to an axis of the scroll roller;
   a data integration apparatus respectively connected to the four probes and configured to be used for data acquisition, analysis and transmission; and
   an electric source connected to the data integration apparatus for providing a working current,
   wherein the wheeled machine is a road compacting machine, the scroll roller is a scrolled wheel of the road compacting machine used for compacting a roadbed, and the data integration apparatus and the electric source are located inside the scroll roller.

2. The test system according to claim 1, wherein a part of the four probes is embedded into the scroll roller, and the detection part protrudes out of an outer surface of the scroll roller.

3. The test system according to claim 2, wherein the four probes present a round-rod-shaped structure, a deep hole is configured on the outer surface of the scroll roller, the probes are fixedly inserted into the deep hole, an outer end of the detection part of the probe protrudes out of an outer surface of the scroll roller.

4. The test system according to claim 3, wherein the probe at least comprises of two parts: an outside part and an inside part, and an outer diameter of the inside part is less than an outer diameter of the outside part, and the structure of the deep hole corresponds to a structure of the probe;

an inner end of a probe protrudes out of inner surface of the scroll roller and is connected with the data integration apparatus.

5. The test system according to claim 4, wherein an insulation gasket, a first nut, a wire terminal, and a second nut are successively configured on the inner end of the probe, the first nut is used for fixing the insulation gasket on the inner surface of the scroll roller, the second nut is used for fixing the wire terminal on the probe, and the wire terminal is used for being connected with the data integration apparatus.

6. The test system according to claim 5, wherein a hard insulation material is configured between the probe and an inner wall of the deep hole.

7. The test system according to claim 6, wherein the hard insulation material is Teflon.

8. The test system according to claim 7, wherein at least a part of surface around the probe is covered with an insulation layer to exclude impact of scroll wheel surface on a measured electric potential.

9. The test system according to claim 8, wherein the data integration apparatus is an integrated circuit used for accurately calculating electrical resistivity and obtaining the water content based on the relationship between a calibrated electrical resistivity and water content of subgrade.

10. The test system according to claim 9, wherein the data integration apparatus has calculation function and wireless transmission function to achieve visualization of water content via a visible mobile device and establish a wireless connection with a intelligent compacted cloud platform, uploading the water content to the cloud platform.

11. The test system according to claim 10, wherein the electric source is a Ni-MH rechargeable battery pack that provides a constant current source for the whole system.

12. A test method for continuously and intelligently measuring water content of subgrade in real-time, wherein the test method is applied to the test system according to claim 1 comprising the following steps:

when a set of electrode gets in touch with soil body, probe A, probe B, probe C and probe D of the set of electrode come into contact with subgrade soil with different water content following the scroll roller of the road compacting machine' moving process, the probe A and probe B are connected to a constant current source, voltage $U_{bc}$ between probe C and probe D, and electric potential difference $U_s$ at both ends of a standard electric resistance $R_s$ are measured through the data integration apparatus so that the test electric resistance can be calculated:

$$R_t = \frac{U_{bc}}{\frac{U_s}{R_s}}$$

ρ can be obtained according to the formula:

$$\rho = \frac{d_{ab}(d_{ab} + d_{bc})}{d_{bc}} \pi R_t$$

where $d_{ab}$ and $d_{bc}$ are distances between the probe A and probe B, the probe B and probe C respectively; $d_{ab}=d_{cd}=nd_{bc}$, where n is a positive integer;

ρ electrical resistivity of subgrade soil is calculated;

the water content is determined according to a relationship between a pre-calibrated electrical resistivity and the water content so that the water content of subgrade soil at any position is obtained.

13. The test method according to claim 12, wherein the test method is applied to the test system wherein a part of the four probes is embedded into the scroll roller, and the detection part protrudes out of the outer surface of the scroll roller.

14. The test method according to claim 13, wherein the test method is applied to the test system wherein the four probes present a round-rod-shaped structure, a deep hole is configured on the outer surface of the scroll roller, the probes are fixedly inserted into the deep hole, an outer end of the detection part of the probe protrudes out of an outer surface of the scroll roller.

15. The test method according to claim 14, wherein the test method is applied to the test system wherein the probe at least comprises of two parts: an outside part and an inside part, and an outer diameter of the inside part is less than an outer diameter of the outside part, and the structure of the deep hole corresponds to a structure of the probe;

an inner end of a probe protrudes out of inner surface of the scroll roller and is connected with the data integration apparatus.

16. The test method according to claim 15, wherein the test method is applied to the test system wherein an insulation gasket, a first nut, a wire terminal, and a second nut are successively configured on the inner end of the probe, the first nut is used for fixing the insulation gasket on the inner surface of the scroll roller, the second nut is used for fixing the wire terminal on the probe, and the wire terminal is used for being connected with the data integration apparatus.

17. The test method according to claim 16, wherein the test method is applied to the test system wherein a hard insulation material is configured between the probe and the inner wall of the deep hole.

18. The test method according to claim 17, wherein the test method is applied to the test system wherein the hard insulation material is Teflon.

19. The test method according to claim 18, wherein the test method is applied to the test system wherein at least a part of surface around the probe is covered with an insulation layer to exclude impact of scroll wheel surface on the measured electric potential.

20. The test method according to claim 19, wherein the test method is applied to the test system wherein the data integration apparatus is an integrated circuit used for accurately calculating electrical resistivity and obtaining the water content based on the relationship between a calibrated electrical resistivity and water content of subgrade.

21. The test method according to claim 20, wherein the test method is applied to the test system wherein the data integration apparatus has calculation function and wireless transmission function to achieve visualization of water content via a visible mobile device and establish a wireless connection with a intelligent compacted cloud platform, uploading the water content to the cloud platform.

22. The test method according to claim 21, wherein the test method is applied to the test system wherein the electric source is a Ni-MH rechargeable battery pack that provides a constant current source for the whole system.

\* \* \* \* \*